United States Patent [19]

Otsuka et al.

[11] Patent Number: 4,608,249

[45] Date of Patent: * Aug. 26, 1986

[54] HYDROPHILIC THERAPEUTIC MATERIAL

[75] Inventors: Saburo Otsuka; Toshiyuki Yoshikawa; Shoichi Tokuda; Yuusuke Ito, all of Osaka, Japan

[73] Assignees: Nitto Electric Industrial Co., Ltd.; Toa Eiyo Litd., both of Japan

[*] Notice: The portion of the term of this patent subsequent to Dec. 13, 2000 has been disclaimed.

[21] Appl. No.: 438,422

[22] Filed: Nov. 2, 1982

[51] Int. Cl.$^4$ .................... A61L 15/03; A61K 31/79; C08F 220/12

[52] U.S. Cl. ........................ 424/28; 424/80; 526/329.5

[58] Field of Search ............... 424/28, 81, 78; 604/307, 892, 896, 897; 526/329.5; 523/111, 118

[56] References Cited

U.S. PATENT DOCUMENTS

| | | | |
|---|---|---|---|
| 2,870,129 | 1/1959 | Merriam | 424/81 |
| 2,884,126 | 4/1959 | Ulrich | 428/355 |
| 3,063,844 | 11/1962 | Meguro et al. | 526/329.5 |
| 3,310,513 | 3/1967 | Barie, Jr. et al. | 526/329.5 |
| 3,575,911 | 4/1971 | Peterson | 524/340 |
| 3,598,122 | 8/1971 | Zaffaroni | 424/28 X |
| 3,697,490 | 10/1972 | Starmer | 526/329.5 |
| 3,699,963 | 10/1972 | Zaffaroni | 604/897 |
| 3,772,063 | 11/1973 | Fukukawa et al. | 117/93.31 |
| 3,927,203 | 12/1975 | Seymour et al. | 424/61 |
| 4,158,053 | 6/1979 | Greene et al. | 424/81 X |
| 4,287,177 | 9/1981 | Nakashima et al. | 424/81 |
| 4,390,520 | 6/1983 | Nagai et al. | 424/28 |
| 4,409,206 | 10/1983 | Stricker | 424/81 |
| 4,420,470 | 12/1983 | Otsuka et al. | 424/28 |

FOREIGN PATENT DOCUMENTS

| | | | |
|---|---|---|---|
| 0043319 | 6/1982 | European Pat. Off. | 424/81 |
| 1952721 | 9/1970 | Fed. Rep. of Germany | 424/63 |
| 7317721 | 7/1974 | Netherlands | 424/81 |

Primary Examiner—Sidney Marantz
Assistant Examiner—Shawn P. Foley
Attorney, Agent, or Firm—Sughrue, Mion, Zinn, Macpeak and Seas

[57] ABSTRACT

A hydrophilic therapeutic material comprising a carrier and a drug-containing patching layer formed thereon directly or indirectly, wherein said patching layer comprises a copolymer of 5 to 75% by weight of an acrylic or methacrylic ester having an ether group in the molecule, 85 to 15% by weight of an alkyl acrylate or alkyl methacrylate and 10 to 50% by weight of a polar monomer copolymerizable therewith.

13 Claims, No Drawings

HYDROPHILIC THERAPEUTIC MATERIAL

FIELD OF THE INVENTION

The present invention relates to a drug-containing hydrophilic therapeutic material adapted to be applied to a lesion of the skin either directly or indirectly by an auxiliary means.

BACKGROUND OF THE INVENTION

A variety of dressing articles have been proposed in the past which comprise a sheet or tape made of a patching agent comprising natural rubber as a main ingredient and a drug such as salicylic esters and menthol. Such dressing articles made of a patching agent comprising natural rubber do not always sufficiently adhere to the skin, or possess sufficient agglutinating or non-irritating properties, transparency, oxidation resistance, etc. As a result, dressing articles made of a patching agent comprising a synthetic resin, such as an acrylate/acrylic acid copolymer, and a drug have been recently proposed.

However, the solubility of the drug in the patching agent of these dressing articles is insufficient and an effective amount of the drug cannot be released within a limited period of time. For example, in a dressing article made of a patching agent comprising an acrylate/acrylic acid copolymer and a corticosteroid as a drug, occasionally only about 5 to 15% of the entire content of the drug can be released within 12 hours. Accordingly, when one wants to release a large amount of an expensive drug within a predetermined period of time, the expensive drug must be included in a large amount which makes the treatment even more expensive. Further, such a dressing article does not absorb sweat on the skin, and does not satisfactorily adhere to the skin. These problems constitute serious drawbacks when using dressing articles containing a drug such as a topical therapeutic agent.

SUMMARY OF THE INVENTION

An object of the present invention is therefore to provide a hydrophilic therapeutic material particularly effective for the treatment of skin lesions, in which a drug (especially a topical therapeutic agent) included in a patching agent can be released at a sufficient rate such that the drug does not crystallize on the skin surface. Since the hydrophilic therapeutic material of the present invention has great water absorbing characteristics, the water absorbed forms a migration route of the drug to the skin and the drug can be released in a large amount within a limited period of time.

Another object of the present invention is to provide a hydrophilic therapeutic material in which a greater portion of a drug present in a patching agent is released within a predetermined period of time with only a very small amount of the drug remaining in the patching agent.

The present invention comprises a hydrophilic therapeutic material comprising a carrier and a drug-containng patching layer formed directly or indirectly thereon, wherein the patching layer comprises a copolymer of 5 to 75% by weight of an acrylic or methacrylic ester having an ether group in the molecule, 85 to 15% by weight of an alkyl acrylate or an alkyl methacrylate and 10 to 50% by weight of a polar monomer copolymerizable therewith.

DETAILED DESCRIPTION OF THE INVENTION

The hydrophilic therapeutic material of the present invention comprises a carrier and a drug-containing patching layer on the carrier wherein the layer has been adapted to be applied in contact with a lesion, and wherein the structure of the patching layer is such as to increase the solubility of the drug therein and the release ratio of the drug.

The acrylic or methacrylic ester having an ether group in the molecule, component (A), is an ester monomer having an ether linkage in the alcohol moiety. The acrylic or methacrylic ester acts to increase the solubility of the drug in the patching layer and to release a large amount of the drug in a limited period of time for the reasons set forth below.

Examples of component (A) include tetrahydrofurfuryl acrylate, tetrahydrofurfuryl methacrylate, methoxypolyethylene glycol acrylate, methoxypolyethylene glycol methacrylate, ethoxydiethylene glycol acrylate, ethoxydiethylene glycol methacrylate, butoxydiethylene glycol acrylate, butoxydiethylene glycol methacrylate, butylene glycol acrylate, butylene glycol methacrylate, methoxyethyl acrylate, methoxyethyl methacrylate, 3-ethoxypropyl acrylate, 3-ethoxypropyl methacrylate, ethoxyethyl acrylate, ethoxyethyl methacrylate, butoxyethyl acrylate, and butoxyethyl methacrylate. Of these compounds, methoxyethyl acrylate, methoxyethyl methacrylate, ethoxyethyl acrylate and ethoxydiethylene glycol acrylate are preferred.

These ester monomers are generally such that their homopolymers have a glass transition temperature of from $-10°$ to $-70°$ C. In addition, the ester monomer units have a free volume permitting free movement of high molecular segments at temperatures at which the hydrophilic therapeutic material is used. Because of the electron donating property of the ether linkage, the diffusion movement of the drug within the copolymer is increased. The combination of these properties with the high solubility of the drug in the ester monomer makes it possible to release the drug in a large amount within a limited period of time.

The alkyl acrylate or alkyl methacrylate, component (B), imparts tackiness, adhesiveness and agglutinating property to the patching agent used in the present invention.

Examples of component (B) include n-butyl acrylate, n-butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, isoamyl acrylate, isononyl acrylate and isononyl methacrylate. Of these compounds, n-butyl acrylate, 2-ethylhexyl acrylate, isooctyl acrylate and isononyl acrylate are preferred.

The mixing ratio of the acrylic or methacrylic ester having an ether group in the molecule (A), the alkyl acrylate or methacrylate (B) and a polar monomer (C) to be described below, i.e., (A):(B):(C), is 5-75:85-15:10-50 in % by weight. If the proportion of component (A) is less than 5% by weight, the drug cannot be easily absorbed in the patching layer, and some drugs may crystallize after mixing with the patching layer. Hence, initially the releasability of the drug is poor and its efficacy decreases quickly. If the proportion of component (A) is above 75% by weight, initially there is sufficient dissolution and release of the drug, but the therapeutic material undesirably has poor adhesiveness when directly applied to the skin.

In preparing the acrylic or methacrylic esteralkyl acrylate or alkyl methacrylate copolymer, 10 to 50% by weight of a polar monomer is copolymerized in the copolymer in order to further increase the agglutinating property of the copolymer in addition to increase the copolymer's hydrophilicity.

Examples of polar monomer as component (C) include functional monomers such as acrylic acid, methacrylic acid, itaconic acid, maleic acid, maleic anhydride, hydroxyethyl acrylate, hydroxypropyl acrylate, acrylamide and dimethyl acrylamide, and vinyl esters such as acrylonitrile, vinyl acetate and vinyl propionate. Of these compounds, vinyl acetate, acrylic acid and hydroxyethyl acrylate are preferred.

The addition of the polar monomer acts to absorb moisture on the skin, increase the adhesion of the therapeutic material to the skin, accelerate diffusion of the drug in the copolymer to the skin, thus increasing its releasability, and to prevent the copolymer from being plasticized, i.e., to prevent the copolymer from having reduced tackiness even when adjuvants, such as those described below, are retained in the copolymer.

A drug is included in a pharmaceutically effective concentration in the copolymer obtained by copolymerizing the acrylic or methacrylic ester having an ether group in the molecule and the alkyl acrylate or alkyl methacrylate. Inclusion of the drug may be effected by dissolving it in the acrylic or methacrylic ester having an ether group or the alkyl acrylate or alkyl methacrylate, or in the copolymer.

In order to release the drug more accurately from the patching layer, increase the efficacy of the released drug, or to obtain both of these functions, at least one adjuvant selected from alcohols such as propylene glycol and diethylene glycol, salicylic acid, urea, allantoin, dimethyl sulfoxide, dimethylacetamide, dimethylformamide, diisopropyl adipate, diethyl sebacate, ethyl laurate, etc., may be added taking into consideration both the composition and efficacy of the drug. The amount of the adjuvant is desirably 0.5 to 20 parts by weight per 100 parts by weight of the copolymer.

Examples of drugs which can be used in the present invention are listed below.

(A) Corticosteroids

Hydrocortisone, prednisolone, paramethasone, beclomethasone propionate, flumethasone, betamethasone, dexamethasone, triamcinolone, triamcinolone acetonide, fluocinolone, fluocinolone acetonide, fluocinolone acetonide acetate and clobetasol propionate.

(B) Analgesics and anti-inflammatory agents

Acetaminophen, mefenamic acid, flufenamic acid, indomethacin, diclofenac, alclofenac, oxyphenbutazone, phenylbutazone, Ibuprofen, flurbiprofen, salicylic acid, methyl salicylate, l-menthol, camphor, and blends of these.

(C) Hypnotic and sedative agents

Phenobarbital, amobarbital, and cyclobarbital.

(D) Tranquilizers

Fluphenazine, thioridazine, diazepam and chloropromazine.

(E) Antihypertensive agents

Clonidine, nifedipine and clonidine hydrochloride.

(F) Hypotensive diuretics

Hydrothiazide, and bendroflumethiazide.

(G) Antibiotics

Penicillin, oxytetracycline, fradiomycin sulfate, erythromycin and chloramphenicol.

(H) Anesthetics

Lidocaine, benzocaine, and ethyl aminobenzoate.

(I) Antimicrobial agents

Benzalkonium chloride, nitrofurazone, nystatin, acetosulfamine and clotrimazole.

(J) Antimycotic agents

Pentamycin, amphotericin B, pyrrolnitrin and clotrimazole.

(K) Vitamin preparations

Vitamin A, ergocalciferol, cholecalciferol, octotiamine and riboflavine butyrate.

(L) Anticonvulsants

Nitrazepam and meprobamate.

(M) Coronary vasodilators

Nitroglycerin, nitroglycol, isosorbide dinitrate, erythrityl tetranitrate and pentaerythrityl tetranitrate.

(N) Antihistaminic agents

Diphenhydramine hydrochloride, chloropheniramine and diphenyl imidazole.

As required, these drugs may be used as a combination of two or more. Among the above drugs, the corticosteroids, analgesic agents and anti-inflammatory agents are preferred. These drugs are included in an amount of about 0.01 to about 20 parts by weight per 100 parts by weight of the total weight of the patching components of the patching later (including the polar monomer to be copolymerized, the adjuvant and other known agents to be added as required). The content of the drug can be freely changed depending upon the drug releasing ability of the patching layer, the composition and efficacy of the drug itself, etc.

The patching layer is formed partly or wholly on a carrier such as a synthetic resin film, sheet or piece, a sheet of paper, a non-woven fabric, a woven fabric, a knitted fabric, a soft metal foil, etc., either directly or indirectly through an undercoating material, such as a tacky adhesive composition composed mainly of rubber and/or a synthetic resin or the abovedescribed copolymer containing no drug. This may be effected by preparing a drug-containing patching composition by emulsion polymerization, solution polymerization, etc., and coating it on the carrier either directly or indirectly and drying the coating; or by first coating the drug-containing patching composition on a release liner and drying it to form a film and then transferring the film onto the carrier.

The patching layer composed of the above-described copolymer used in the hydrophilic therapeutic material of the present invention is non-irritating to the skin even when it is applied directly or indirectly, i.e., with the aid of an auxiliary means such as a surgical adhesive tape, to the surface of a lesion for a long period of time.

The ratio between the acrylic or methacrylic ester having an ether group in the molecule in the copolymer and the amounts of the polar monomer to be copolymerized to increase the agglutinating property and hydrophilicity, and the amount of the adjuvant to be added, may vary depending upon the composition of the drug for obtaining the desired pharmaceutical effect.

The present invention is now described in greater detail by reference to the following examples which are given for illustrative purposes only and are by no means intended to limit the scope of the invention. All parts in these examples are by weight.

EXAMPLE 1

| | |
|---|---|
| Methoxyethyl Acrylate | 50 parts |
| Isooctyl Acrylate | 25 parts |
| Vinyl Acetate | 25 parts |
| Ammonium Persulfate | 0.2 part |
| Water | 150 parts |
| Emulsifying Agent (octyl phenoxy ethanol; ethylene oxide units = 30) | 4 parts |

A mixture of the above ingredients was charged into a four-neck flask and heated to a reaction temperature of 60° to 63° C. for 4 hours in an inert gas atmosphere. The reaction mixture was aged at 80° C. for 2 hours to obtain a copolymer solution having a viscosity (measured by a BH-type rotary viscometer at a speed of 4 rpm) determined for its 40% solution of 48 poises at a polymerization conversion of 99.5%.

The copolymer solution was mixed with salicylic acid emulsified by an emulsifying agent. The mixture was coated on the surface of a polyethylene film so that the thickness of the coating after drying was 50μ. The coating was dried at 80° C. for 7 minutes to produce a pharmaceutical material in accordance with the present invention. The amount of salicylic acid was 200μg/cm² at the above-described thickness.

EXAMPLE 2

| | |
|---|---|
| Tetrahydrofurfuryl Acrylate | 10 parts |
| iso-Octyl Acrylate | 70 parts |
| Hydroxypropyl Acrylate | 20 parts |
| Azobisisobutyronitrile | 0.1 part |
| Ethyl Acetate | 25 parts |

A mixture of the above ingredients was charged into a four-neck flask and heated at a temperature of 60° to 63° C. in an inert gaseous atmosphere with stirring. While adding dropwise 125 parts of ethyl acetate, the reaction temperature was controlled and the reaction was performed for 10 hours. Then, the reaction mixture was aged for 2 hours at 75° to 80° C. to yield a copolymer solution having a viscosity, determined for its 40% ethyl acetate solution, of 650 poises at a polymerization conversion of 94.5%.

Prednisolone was added to the copolymer solution and the mixture was coated on a polyethylene film so that the thickness of the coating after drying was 50μ. The coating was dried at 80° C. for 5 minutes to produce a hydrophilic pharmaceutical material in accordance with the present invention. The amount of prednisolone was 30 μg/cm² at the aforesaid thickness.

EXAMPLE 3

| | |
|---|---|
| Ethoxyethyl Acrylate | 20 parts |
| 2-Ethylhexyl Acrylate | 65 parts |
| Acrylic Acid | 15 parts |
| Benzoyl Peroxide | 0.2 part |
| Ethyl Acetate | 25 parts |

A mixture of the above ingredients was reacted in the manner as in Example 2 to yield a copolymer solution having a viscosity, determined for its 40% solution, of 880 poises at a polymerization conversion of 97%. A hydrophilic pharmaceutical therapeutic material containing 300 μg/cm2 of methyl salicylate was prepared in the same manner as in Example 2 using the resulting copolymer solution.

EXAMPLE 4

| | |
|---|---|
| Ethoxydiethylene Glycol Acrylate | 20 parts |
| Decyl Acrylate | 65 parts |
| 2-Hydroxyethyl Acrylate | 15 parts |
| Benzoyl Peroxide | 0.2 part |
| Ethyl Acetate | 25 parts |

Using a mixture of the above ingredients, a copolymer solution having a viscosity, determined for its 40% solution, of 920 poises at a polymerization conversion of 93.8% was prepared, and a hydrophilic therapeutic material containing 30 μg/cm² of prednisolone was produced, in the same manner as in Example 2.

COMPARATIVE EXAMPLES 1 TO 4

Samples were prepared in the same manner as in the above Examples except that the monomers used were substituted by the following monomers:

Sample No. 1 was obtained by substituting methoxyethyl acrylate of Example 1 with isooctyl acrylate (Comparative Example 1).

Sample No. 2 was obtained without adding hydroxypropyl acrylate in Example 2 (Comparative Example 2).

Sample No. 3 was prepared by substituting ethoxyethyl acrylate of Example 3 with 2-ethylhexyl acrylate (Comparative Example 3).

Sample No. 4 was prepared in the same manner as in Example 4 except that the amount of 2-hydroxyethyl acrylate was changed to 5 parts, and the amount of decyl acrylate was changed to 75 parts (Comparative Example 4).

Table 1 summarizes the results of tests conducted on the therapeutic materials obtained in Examples 1 to 4 and Comparative Examples 1 to 4.

TABLE 1

| Example and Comparative Example | Drug | Adhesiveness | Release Ratio (%) | Inhibition of Carrageenin Foot Edema (%) | Adhesion during Sweating | Water Absorption (after 2 hrs) (%) |
|---|---|---|---|---|---|---|
| Example 1 | Salicylic acid | o | 75 | 42 | Excellent | 32 |
| Comparative | Salicylic | Δ | 41 | 20 | Fair | 9 |

TABLE 1-continued

| Example and Comparative Example | Drug | Adhesiveness | Release Ratio (%) | Inhibition of Carrageenin Foot Edema (%) | Adhesion during Sweating | Water Absorption (after 2 hrs) (%) |
| --- | --- | --- | --- | --- | --- | --- |
| Example 1 | acid | | | | | |
| Example 2 | Prednisolone | o | 61 | 60 | Good | 17 |
| Comparative Example 2 | " | | 30 | 34 | Fair | 7 |
| Example 3 | Methyl salicylate | o | 63 | 55 | Good | 23 |
| Comparative Example 3 | Methyl salicylate | | 37 | 33 | Fair | 2 |
| Example 4 | Prednisolone | o | 69 | 58 | Excellent | 31 |
| Comparative Example 4 | " | | 57 | 47 | Good | 19 |

The various properties shown in Table 1 were measured and evaluated by the following methods.

METHOD OF EVALUATING ADHESIVENESS

A square test sample, 4×4 cm, was attached to the inside of an upper arm and the state of adhesion of the sample to the skin was visually evaluated 24 hours later using the following criteria.
: No peeling occurred at the terminal and upon removing the sample, the hair was pulled off along with the sample.
o: Scarcely any peeling occurred at the terminal and upon removing the sample, the hair was not pulled off along with the sample.
Δ: Peeling occurred at the terminal.
x : More than one-third of the sample peeled off.

METHOD OF MEASURING THE RELEASE RATIO OF THE DRUG

A sheet, 4×4 cm, was prepared, and dipped in 200 ml of water at 30° C. The sample of water containing the sheet was shaken and 1 ml of water was sampled periodically. The sampled water containing the drug was analyzed by a high-performance liquid chromatographic device (UV). The release ratio of the drug was determined by taking the initial content of the drug as 100%. The release ratios given in Table 1 were obtained after 3 hours of dipping.

METHOD OF EVALUATING PHARMACEUTICAL EFFICACY

Pharmaceutical efficacy was evaluated by the inhibition ratio of carrageenin foot edema. HLA-Wistar strain male rats having a body weight of 170 to 200 g were used, six per group as experimental animals.
The volume of the right hind paw of each rat was measured and then a sample, patch 1×2 cm, was adhered onto the right hind paw. The sample was removed after 2 hours and 0.05 ml of a 1% solution of carrageenin in physiological saline was injected subcutaneously in the same right hind paw. Three hours after injection of the carrageenin, the volume of the right hind paw was measured. The difference between the volume of the right hand paw before and after the patching of the sample piece was defined as the volume of foot edema.

$$\text{Ratio of Inhibition of Foot Edema (\%)} = \frac{V_c - V_t}{V_c} \times 100$$

where $V_c$ represents the average volume of foot edema in a control group and $V_t$ represents the average volume of foot edema in the group in which the test sample patch was adhered.

ADHESION DURING SWEATING

The sample was attached to the arm of a person. Ten minutes later, the person was placed in a constant temperature chamber kept at 40° C. for a period of 20 minutes. After the 20 minute period, the state of adhesion of the sample was visually evaluated.

WATER ABSORPTION

A sample, 4×4 cm, was dipped in water at 250° C. After 2 hours its increase in weight was measured.

As can be seen from the above Examples, the hydrophilic therapeutic material of the present invention released greater than 50% of the drug contained in the patching layer containing a copolymer derived from an acrylic or methacrylic ester having an ether group in the molecule as one unit. Further, it is evident that the release was effected within a limited period of time. In addition, the above Examples show that the therapeutic material of the present invention has moderate hydrophilicity and adhesion to the skin and a sufficient pharmaceutical efficacy on skin lesions.

EXAMPLES 5 TO 9 AND COMPARATIVE EXAMPLES 5 TO 9

Each of the samples was prepared in the same manner as in the Examples and Comparative Examples as shown in Table 2 except for varying the drug, the amount of drug and the dry thickness of the coating.
Table 2 summarizes the results of tests conducted on the therapeutic materials obtained in Examples 5 to 9 and Comparative Examples 5 to 9.

TABLE 2

| Example and Comparative Example | Preparation of Therapeutic Material | Drug | Amount of Drug (μg/cm²) | Dry Thickness of Coating (μ) | Release Ratio (%) | Percent Transfer in Skin (%) |
| --- | --- | --- | --- | --- | --- | --- |
| Example 5 | Example 2 | Diazepam | 100 | 50 | 61 | 7 |
| Comparative Example 5 | Comparative Example 2 | " | " | " | 53 | 2 |
| Example 6 | Example 3 | Nifedipine | " | " | 49 | 13 |
| Comparative Example 6 | Comparative Example 3 | " | " | " | 40 | 3 |

TABLE 2-continued

| Example and Comparative Example | Preparation of Therapeutic Material | Drug | Amount of Drug (μg/cm²) | Dry Thickness of Coating (μ) | Release Ratio (%) | Percent Transfer in Skin (%) |
|---|---|---|---|---|---|---|
| Example 7 | Example 3 | Lidocaine | 400 | " | 54 | 19 |
| Comparative Example 7 | Comparative Example 3 | " | " | " | 41 | 9 |
| Example 8 | Example 4 | Isosorbide nitrate | 300 | 40 | 58 | 24 |
| Comparative Example 8 | Comparative Example 4 | Isosorbide nitrate | " | " | 40 | 17 |
| Example 9 | Example 4 | Diphenhydramine hydrochloride | 100 | " | 72 | 20 |
| Comparative Example 9 | Comparative Example 4 | Diphenhydramine hydrochloride | " | " | 61 | 11 |

METHOD OF EVALUATING PERCENT TRANSFER IN SKIN

A sample was punched into a disk having a diameter of 6 cm. The disk was adhered onto the inside of an upper arm for 10 hours. The amount of the drug decreased is expressed by percent based on the initial drug amount, 100%.

The drug content in the sample was measured using a high speed liquid chromatography or gas chromatography after extracting with methanol.

While the invention has been described in detail and with reference to specific embodiments thereof, it will be apparent to one skilled in the art that various changes and modifications can be made therein without departing from the spirit and scope thereof.

What is claimed is:

1. A hydrophilic therapeutic material comprising a backing and a drug-containing patching layer formed thereon directly or indirectly, wherein said patching layer comprises a copolymer of 5 to 75% by weight of an acrylic or methacrylic ester having an ether group in the molecule and having a glass transition temperature of from −10° C. to −70° C., 85 to 15% by weight of an alkyl acrylate or alkyl methacrylate, each alkyl group having from 4 to 13 carbon atoms, and 10 to 50% by weight of a functional monomer copolymerizable therewith.

2. A hydrophilic therapeutic material as in claim 1, wherein said backing is selected from the group consisting of a synthetic resin film, a sheet of paper, a nonwoven fabric, a woven fabric, a knitted fabric, and a soft metal foil.

3. A hydrophilic therapeutic material as in claim 1, wherein said drug-containing patching layer is applied to a lesion of the skin indirectly with the aid of an auxiliary adhesive means.

4. A hydrophilic therapeutic material as in claim 3, wherein said auxiliary means is surgical adhesive tape.

5. A hydrophilic therapeutic material as in claim 1, wherein said ether substituted acrylate or methacrylate ester is selected from the group consisting of tetrahydrofurfuryl acrylate, tetrahydrofurfuryl methacrylate, methoxypolyethylene glycol acrylate, methoxypolyethylene glycol methacrylate, ethoxydiethylene glycol acrylate, ethoxydiethylene glycol methacrylate, butoxydiethylene glycol acrylate, butoxydiethylene glycol methacrylate, butylene glycol acrylate, butylene glycol methacrylate, methoxyethyl acrylate, methoxyethyl methacrylate, 3-ethoxypropyl acrylate, 3-ethoxypropyl methacrylate, ethoxyethyl acrylate, ethoxyethyl methacrylate, butoxyethyl acrylate and butoxyethyl methacrylate.

6. A hydrophilic therapeutic material as in claim 1, wherein said alkyl acrylate or alkyl methacrylate is selected from the group consisting of nbutyl acrylate, n-butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate and tridecyl methacrylate.

7. A hydrophilic therapeutic material as in claim 1, wherein the functional monomer is selected from the group consisting of acrylic acid, methacrylic acid, itaconic acid, maleic acid, maleic anhydride, hydroxyethyl acrylate, hydroxypropyl acrylate, acrylamide, dimethyl acrylamide and vinyl ester such as acrylonitrile, vinyl acetate and vinyl propionate.

8. A hydrophilic therapeutic material as in claim 7, wherein said vinyl ester is selected from the group consisting of acrylonitrile, vinyl acetate and vinyl propionate.

9. A hydrophilic therapeutic material as in claim 1, comprising 0.5 to 20 parts by weight of a pharmaceutically acceptable adjuvant, per 100 parts by weight of said copolymer.

10. A hydrophilic therapeutic material as in claim 9, wherein the adjuvant is at least one member selected from the group consisting of propylene glycol, diethylene glycol, salicylic acid, urea, allantoin, dimethyl sulfoxide, dimethylacetamide, dimethylformamide, diisopropyl adipate, diethyl sebacate and ethyl laurate.

11. A hydrophilic therapeutic material as in claim 1, wherein the drug contained in the patching layer is at least one member selected from the group consisting of corticosteroids, analgesics, antiinflammatory agents, hypnotic agents, sedative agents, tranquilizers, antihypertensive agents, hypotensive diuretics, antibiotics, anesthetics, antimicrobial agents, antimycotic agents, vitamin preparations, anticonvulsants, coronary vasodilators and antihistaminic agents.

12. A hydrophilic therapeutic material as in claim 1, wherein the drug contained in the patching layer is at least one member selected from the group consisting of corticosteroids, analgesics and anti-inflammatory agents.

13. A hydrophilic therapeutic material as in claim 1, wherein the drug contained in the patching layer is in an amount of 0.01 to 20 parts by weight per 100 parts by weight of all of the components of the patching layer.

* * * * *